United States Patent [19]
Hübner

[11] Patent Number: 5,108,702
[45] Date of Patent: Apr. 28, 1992

[54] BLOOD AERATOR

[76] Inventor: Karl-Alexander Hübner, Kanalstrasse 17-19, D-7504 Weingarten, Fed. Rep. of Germany

[21] Appl. No.: 389,509

[22] Filed: Aug. 4, 1989

[30] Foreign Application Priority Data

Aug. 20, 1988 [DE] Fed. Rep. of Germany ... 8810552[U]
Feb. 10, 1989 [DE] Fed. Rep. of Germany ... 8901513[U]

[51] Int. Cl.$^5$ .............................................. A61M 1/14
[52] U.S. Cl. ..................................... 422/45; 436/168;
436/178; 210/221.2; 210/416.1; 210/432;
210/456; 604/411; 604/415; 604/416; 128/763;
128/764; 128/DIG. 3
[58] Field of Search ................... 422/44, 45, 47, 102,
422/103; 436/168, 178; 210/150, 205, 221.2,
416.1, 432, 456; 604/4, 411, 403, 415, 416;
128/DIG. 3, 760, 763, 764

[56] References Cited

U.S. PATENT DOCUMENTS

| 3,175,555 | 3/1965 | Ling | 422/47 |
| 3,467,095 | 9/1969 | Ross | 422/44 X |
| 3,492,991 | 2/1970 | Dyer, Jr. | 422/44 X |
| 3,664,814 | 5/1972 | Koremura | 422/44 |
| 4,639,316 | 1/1987 | Eldegheidy | 210/416.1 |
| 4,810,378 | 3/1989 | Carmen et al. | 210/206 |

Primary Examiner—Lynn M. Kummert
Attorney, Agent, or Firm—Dvorak and Traub

[57] ABSTRACT

A blood aerator comprises an aerating vessel having a vessel body provided with ports for a gas- and liquid-tight connection to a blood hose and at least one gas hose. A simplified and reliable handling is permitted in that a port for the blood hose and a port for a lower gas hose are separately provided on the bottom portion of the vessel body, the port for the lower gas hose contains a hydrophobic filter element, which is impermeable to blood and permeable to gas, and the port for a second gas hose is provided on the top portion of the vessel body.

2 Claims, 3 Drawing Sheets

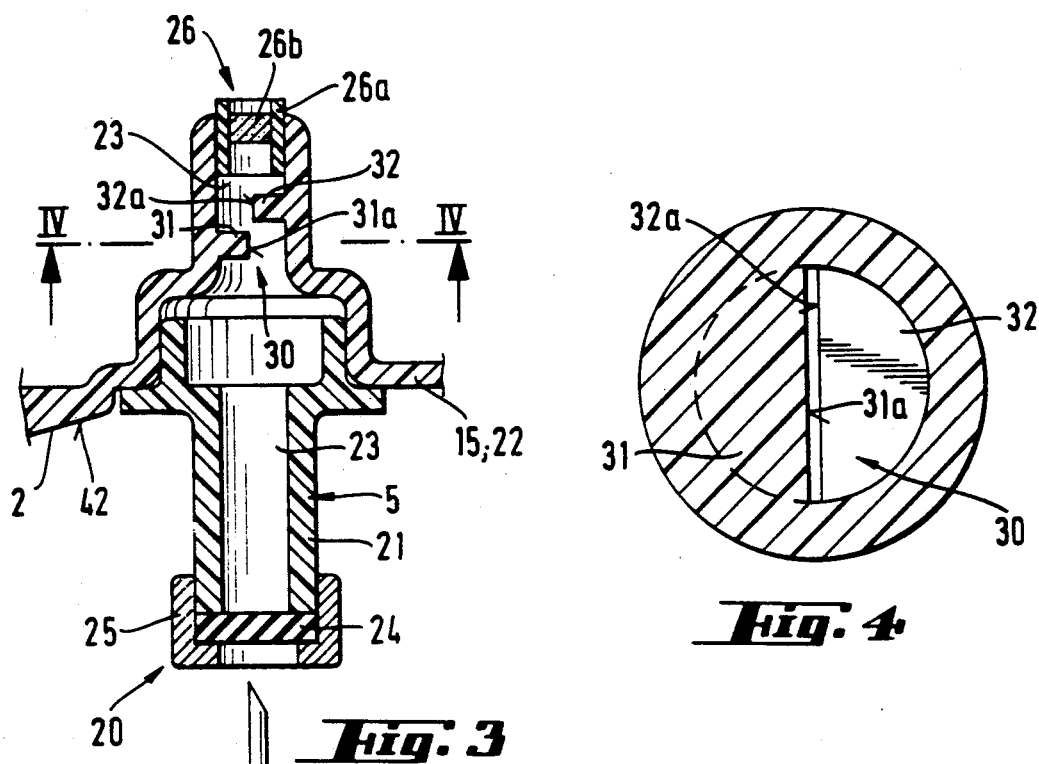
Fig. 3
Fig. 4
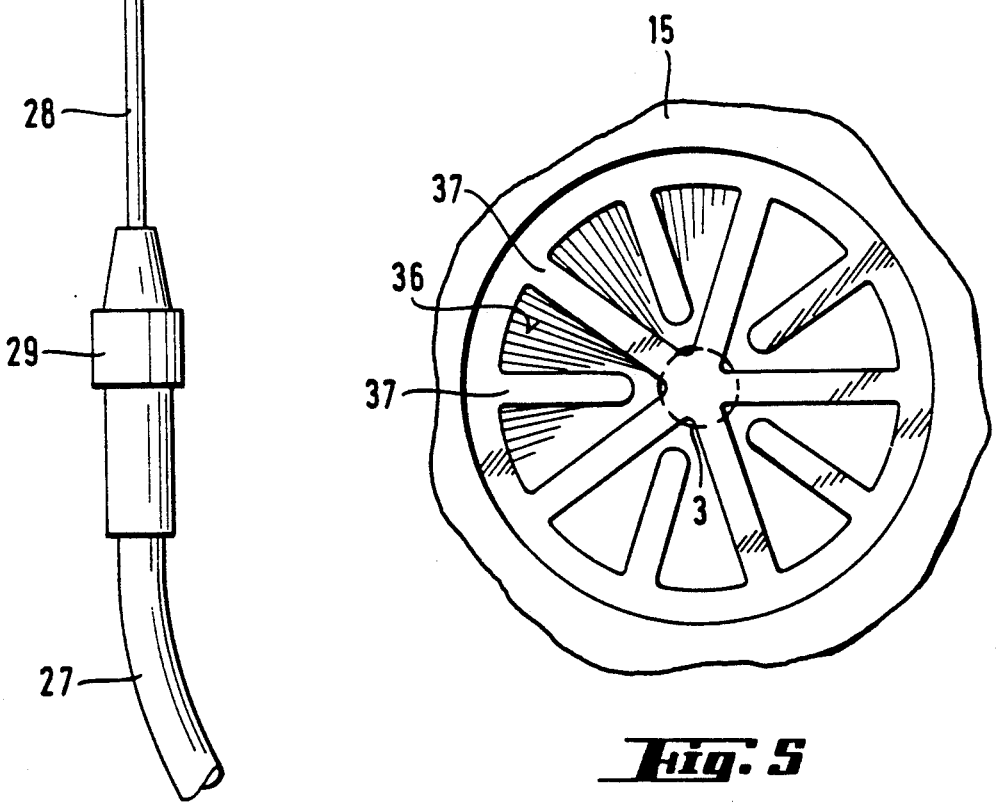
Fig. 5

BLOOD AERATOR

BACKGROUND OF THE INVENTION

1. Field of the Invention

This invention relates to a blood aerator comprising an aerating vessel having a vessel body provided with port means for a gas- and liquid-tight connection to a blood hose and at least one gas hose.

2. Description of the Prior Art

Such blood aerators are used mainly for the ozonization of blood in autohemotherapy. In that case the blood is supplied into the previously evacuated aerating vessel and is aerated in said vessel and is subsequently infused. For the sake of simplicity only the aeration with ozone will be referred to hereinafter although the aerator in accordance with the invention can be used also for other processes of aerating blood.

In the previous practice, the usual infusion bottles made of glass have been used, which comprise a tubular port that is sealed by a plug made of silicone rubber.

A connection to the patient is made by means of an infusion set, which is introduced into the plug of silicone rubber. The connection to the gas source, usually consisting of an ozonizer, is made by means of a so-called Heidelberger conduit, which is also inserted into the silicone plug. A venting hose is also provided and, optionally, a cannula for a supply of medicaments which may be required and may particularly consist of anticoagulants.

That known aerator can be handled only with great difficulty. Specifically, the various connecting means must be very exactly inserted into the plug. In the usual bottles, the plug is only about 3 cm in diameter. The infusion set alone is about 2 cm in diameter. It must also be kept in mind that the gas supply line is usually connected to an aerating tube, which is immersed almost to the bottom of the bottle. When that tube is damaged owing to the confined space, blood may enter the aerator during the suction phase and may effect considerable damage to the aerator.

SUMMARY OF THE INVENTION

It is an object of the invention to provide a blood aerator which can be handled in a simpler manner and with higher reliability.

In a blood aerator which is of the kind described first hereinbefore that object is accomplished in that a port for the blood hose and a port for a lower gas hose are separately provided on the bottom portion of the vessel body, the port for the lower gas hose contains a hydrophobic filter element, which is impermeable to blood and permeable to gas, and a port for a second gas hose is provided on the top portion of the vessel body.

The several features of the blood aerator in accordance with the invention are closely interrelated. In the first place, the provision of the port for connection to a blood hose and the port for connection to a lower gas hose, which ports suitably consist of two separate tubular ports, has the result that the aerator can be handled without the difficulties mentioned above. In the second place it is essential that the mouth of the port for connection to a blood hose is disposed on the lower portion of the vessel body at a location which is below the level of the blood which is being aerated. This is permitted by the use of the hydrophobic filter element.

Blood vessels provided with ports for connection to hoses in numerous different arrangements have already been proposed for other applications. Examples are apparent from U.S. Pat. No. 4,443,220, East German Patent 202,391, Published German Application 29 20 283 and the French patent application published under No. 2,258,192. But as none of said printed publications relates to a blood aerator, they do not furnish a suggestion toward the present invention. Moreover, none of said printed publications discloses the use of a hydrophobic filter.

The blood aerator in accordance with the invention can be operated in a manner which is basically different from the operation of the devices known in the art and can be handled in a simpler manner. For a taking of blood, the known infusion bottles are suspended with the plug at the bottom, and the blood is aerated in an inverted position with the plug at the top and with the end of the above-mentioned aerating tube disposed below the level of the blood. As a result, the gas was bubbled through the blood. For another infusion, the bottle had again to be suspended with the plug at the bottom.

In the use of the aerator in accordance with the invention the aerating vessel can remain in the same position, in which it is suitably suspended from an infusion set, also during the aeration of the blood so that several handling steps can be omitted.

The vessel body suitably consists of plastic. In a particularly favorable arrangement the blood hose and the upper gas hose are permanently joined, preferably by adhesive, to the associated ports. In that case the aerating vessel and the blood hose constitute a discardable article, which is ready for use and which may suitable have been evacuated in the factory.

BRIEF DESCRIPTION OF THE DRAWING

FIG. 3 shows the portion designated III in FIG. 1 and the end of a gas hose provided with an insertable cannula for the injecting valve.

FIG. 4 is a transverse sectional view taken on line IV—IV in FIG. 3 and showing an admixing valve.

FIG. 5 shows a port for a blood hose viewed from the interior of the aerating vessel.

DETAILED DESCRIPTION OF THE PREFERRED EMBODIMENT

Figure 1:
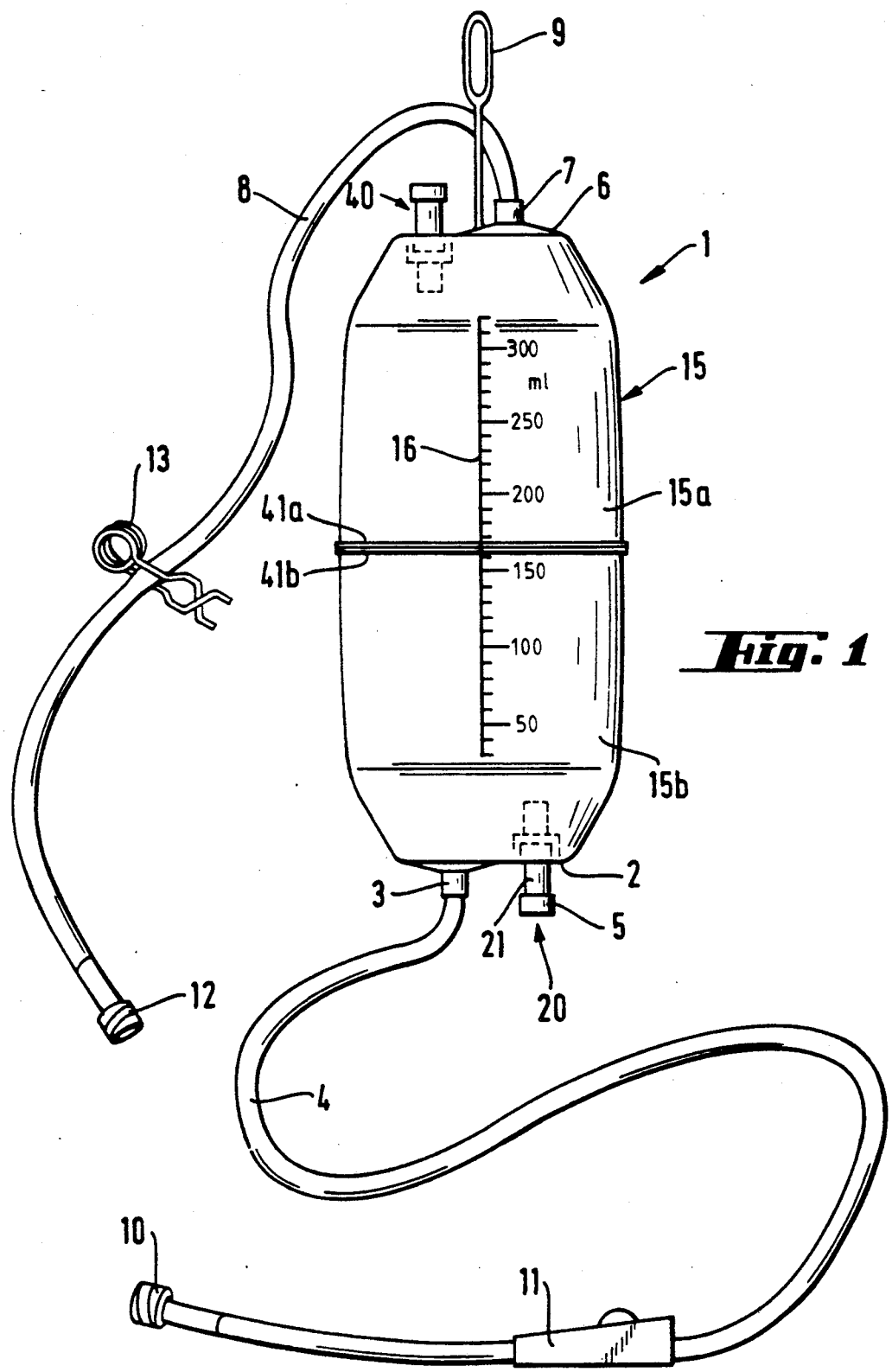
FIG. 1 is a blood aerator which embodies the invention.

The invention will be explained more in detail hereinafter with reference to an illustrative embodiment which is diagrammatically shown in the drawings.

The aerating vessel 1 of the blood aerator shown in FIG. 1 is provided on its bottom portion 2 with a tubular port 3 for connection to a blood hose 4 and with a tubular port 5 for connection to a lower gas hose, which is not shown here.

The aerating vessel 1 is provided on its top portion 6 with a tubular port 7, which is connected to a second gas hose 8.

The statement that the ports for connection to the blood and gas hoses are provided "on the bottom portion" and "on the top portion" of the aerating vessel 1 does not mean that said ports must be connected to the vessel at its bottom and top, respectively. Each of said ports may be laterally, e.g., radially connected, provided that the lower gas port 5 is below the lowest blood level to be expected in practice and the upper gas port 7 is disposed above the highest blood level to be expected in practice.

The aerating vessel 1 is provided with a hanger eyelet 9, which is suitably integrally injection molded with the vessel 1 and in the use of said vessel 1 is used to suspend the vessel 1 from an infusion set, not shown. The blood hose 4 is provided at its free end with a suitable coupling 10, which consists, e.g., of a Luerlock connector, for connection to an infusion needle for withdrawing blood from a patient. The suction rate may be controlled by means of a roller clamp 11, which is usual in infusion practice.

The vacuum which is required in the aerating vessel 1 for a sucking of blood can be produced by an extraction of air through the upper gas hose 8, which is suitably also provided with a Luerlock connector 12 for connection to a suitable apparatus.

But the blood aerator will preferably be evacuated in the factory and be placed at the disposal of the user as a discardable article which is ready for use. For that purpose the blood hose 4 is sealed by means of a roller clamp 11, which is vacuum-tight in a closed state. The gas hose 8 is shut off by a vacuum-tight clamp 13. The hoses 4, 8 are permanently joined to the associated ports 3 and 7, e.g., by an adhesive. It will be understood that the vessel body 1 is entirely vacuum-tight.

The vessel body 15 of the vessel 1 suitably consists of a transparent plastic, particularly of an acryl glass, such as polymethyl methacrylate, and is provided with a scale 16, from which the quantity of blood which has been sucked can easily be read.

When blood in the quantity required for an intended treatment has been sucked into the vessel body 1, the blood is aerated. This may be effected by either of two different methods, which may easily be carried out with the blood aerator in accordance with the invention.

In the so-called hyperbaric ozonization, ozone under a slightly superatmospheric pressure is supplied into the gas space over the surface of the blood. This is effected by means of the hose 8, which is connected by the coupling 12 to a suitable apparatus, such as the apparatus which is available under the name "Humazon" from Technomed GmbH, Weingarten, West Germany.

For a normal ozonization the gas is bubbled through the blood. In that case a gas hose, not shown here, is connected to the lower gas hose port 5 and the gas is bubbled through the blood and escapes through the upper gas hose 8. The passage opening of the gas hose port 5 contains a hydrophobic filter element, which permits the gas to flow from the outside into the interior of the aerating vessel and is impermeable for blood.

Such hydrophobic filter elements are commercially available for other applications. A suitable product is available, e.g., under the name 0.2 μm Hydrophob from Schleicher & Schuell, 3354 Dassel, West Germany. But within the scope of the invention it is possible to use any filter element which is permeable to gas, impermeable to blood and physiologically acceptable.

The connection of a gas supply hose to the gas hose port 5 may be effected in various ways, e.g., also by means of a Luerlock connector. In a particularly preferred embodiment the connection is made by means of an injecting valve, such as is shown in an enlarged view in FIG. 3.

The admixing valve 20 comprises a tube 21, which is gas-tightly inserted into the wall 22 of the vessel body 15, e.g., by means of an adhesive. The passage 23 of the tube 21 is closed on the outside by a piercable gasket plate 24 made of rubber-elastic material. That gasket plate 24 is tightly joined to the tube 21, e.g., by means of a clamp ring 25, as shown.

The passage 23 is formed in the present embodiment by an inwardly bulging portion of the wall 22 and is closed toward the interior of the vessel 1 by the hydrophobic filter element 26. The illustrated filter element 26 consists of a plastic sleeve 26a and of a hydrophobic filter 26b, which is held in the sleeve 26a and has the above-mentioned permeability properties. The seal between the hydrophobic filter element 26 and the inside surface of the tube 21 may be effected by an interference fit or, for higher safety, by an adhesive joint.

FIG. 3 shows diagrammatically also the end of a lower gas hose 27, which is provided at that end with a piercing cannula 28. The connection between the gas hose 27 and the vessel can simply be made in that the piercable gasket 24 is pierced by the cannula 28.

In that case it is of special importance to reliably prevent the pointed cannula 28 from damaging the hydrophobic filter element 26 so that blood might enter the ozonizer. For that reason the admixing valve 20 comprises stop means 30 for limiting the depth to which an element for piercing the gasket 24 can be inserted. For that purpose the tube 21 may be longer than the cannula 28, which has a head 29 that is necessarily larger in diameter than the passage 23 and which strikes against the tube 21 to limit the depth to which an element for piercing the gasket 24 can be inserted. But a limitation cannot be effected by such an arrangement unless the length of the tube and the lenght of the cannula 28 which are employed are properly related to each other.

Figure 2:
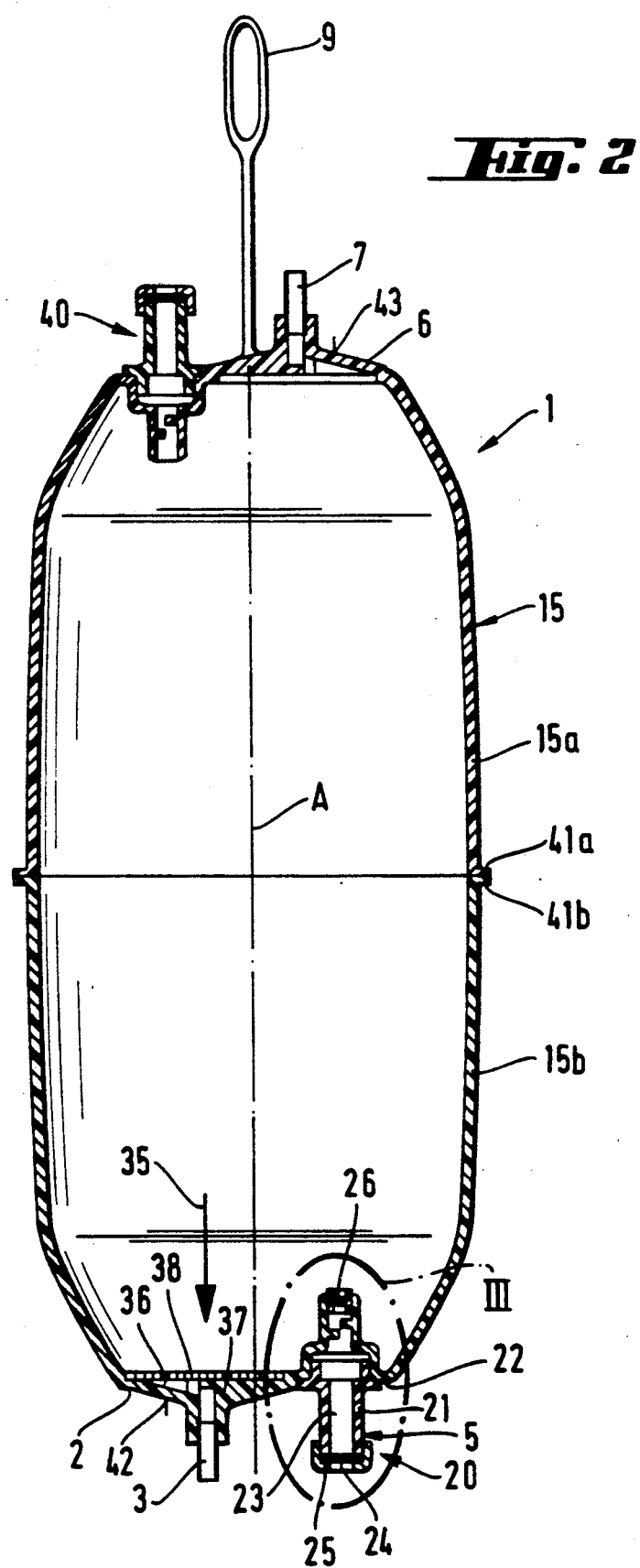
FIG. 2 is a longitudinal sectional view showing an aerating vessel of an aerator as shown in FIG. 1.

It is preferable to limit the piercing movement by means 30 comprising at least two stops 31, 32, which protrude into the passage 23 and are axially spaced apart, as is apparent form FIGS. 2 and 3. From the aspect of injection molding technology it will be desirable to arrange the inner edges 31a and 32a (FIG. 4) of the stops 31, 32 in the same plane, which is parallel to the axis of the tube 21.

FIG. 5 is a view that is taken in the direction indicated by the arrow 35 in FIG. 2 on the mouth of the tubular port 3 for the blood hose. The tubular port 3 flares toward the interior of the vessel in the form of a funnel 36. Radially extending fins 37 serve to support a filter sieve 38 (FIG. 2), which at its rim is joined to the vessel body 15 by a welded joint or adhesive.

The vessel body 15 desirably consists of two identical parts 15a and 15b. The upper gas hose port 7 is designed like the blood hose port 3 but the filter sieve 38 is not required and can be omitted. A second admixing valve 40 is suitably provided at the top end of the vessel 1 and is designed like the first admixing valve 20 but has no hydrophobic filter element. Such valve may be used, e.g., for a supply of medicaments, particularly anticoagulants, by means of a syringe.

Two identical parts 15a and 15b can easily and reliably be joined by adhesive or by a welded joint because the connecting flanges 41a, 41b are specially designed. Each of said flanges consists of two portions, which have different shapes in cross-section. Each flange has a projecting profile in one half of its periphery and the other half has a mating recessed profile in the same diameter range.

The vessel body 15 having the shape shown in FIG. 2 has also proved to be suitable. If the vessel body 15 has the substantially cylindrical shape which is shown, its end faces 42, 43, which extend at right angles to the axis A, are desirably relatively small and gradually merge by a rounded portion into that portion of the vessel body which has the full diameter. But the invention is not restricted in its broadest scope to a substantially cylindrical vessel body.

I claim:

1. In a blood aerator comprising an aerating vessel having a vessel body that includes top and bottom portions and is provided with port means for gastight connections to a blood hose and at least one gas hose, the improvement residing in that said port means comprise means defining a first port, which is provided at said bottom portion and connectable to a blood hose, said first port being provided with a filter sieve, means defining a second port, which is provided at said bottom portion and is separate from said first port and connectable to a lower gas hose and contains a hydrophobic filter element, which is impermeable to blood and permeable to gas. and means defining a third port, which is provided at said top portion and connectable to an upper gas hose, wherein said second port comprises an admixing valve that comprises a pierceable gasket made of rubber-elastic material, wherein said admixing device is provided with stop means for limiting the depth to which an element which is used to pierce said gasket can be inserted into said valve, and wherein said second port is tubular and defines a passage containing said admixing valve, and said stop means comprise at least two stops, which are spaced apart in an axial direction of said second port and protrude into said passage.

2. The improvement set forth in claim 1, wherein said vessel body consists of two identical top and bottom sections, which comprise said top and bottom portions, respectively.

* * * * *